United States Patent [19]

Devic

[11] Patent Number: 4,591,460

[45] Date of Patent: May 27, 1986

[54] PROCESS FOR THE DECOMPOSITION OF A COMPLEX OF ORTHOBENZOYL-BENZOIC ACID, HYDROGEN FLUORIDE AND BORON TRIFLUORIDE

[75] Inventor: Michel Devic, Lyons, France

[73] Assignee: Atochem, France

[21] Appl. No.: 590,861

[22] Filed: Mar. 19, 1984

[30] Foreign Application Priority Data

Mar. 30, 1983 [FR] France ................. 83 05207

[51] Int. Cl.$^4$ ............................................. C07C 50/18
[52] U.S. Cl. ......................................... 260/369
[58] Field of Search ................................. 260/369

[56] References Cited

U.S. PATENT DOCUMENTS

| | | | |
|---|---|---|---|
| 3,032,560 | 5/1962 | Dawsey ................. | 260/369 |
| 4,035,396 | 7/1977 | Milano ................. | 260/369 |
| 4,045,456 | 8/1977 | Merger et al. ......... | 260/369 |
| 4,087,458 | 5/1978 | Emori et al. .......... | 260/369 |

FOREIGN PATENT DOCUMENTS

| | | | |
|---|---|---|---|
| 0055951 | 7/1982 | European Pat. Off. ... | 260/369 |
| 2532303 | 3/1984 | France ................ | 562/460 |

*Primary Examiner*—Glennon H. Hollrah
*Assistant Examiner*—Raymond Covington
*Attorney, Agent, or Firm*—Sigalos & Levine

[57] ABSTRACT

Process for the decomposition of complexes of ortho-benzoyl-benzoic acid, hydrogen fluoride, and boron trifluoride in which the complex is subjected to the action of sulfuric acid in a concentration of at least about 96% by weight or to the action of an oleum, under atmospheric pressure or under a pressure lower than atmospheric pressure.

10 Claims, 1 Drawing Figure

PROCESS FOR THE DECOMPOSITION OF A COMPLEX OF ORTHOBENZOYL-BENZOIC ACID, HYDROGEN FLUORIDE AND BORON TRIFLUORIDE

BACKGROUND OF THE INVVENTION

The present invention relates to a process for the decomposition of complexes formed from orthobenzoyl-benzoic acid (OBB acid), hydrogen fluoride (HF) and boron trifluoride (BF$_3$), of the general formula:

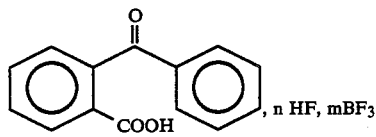

in which n and m are between 1 and 6.

Such complexes can be obtained according to the European Patent Application No. 0,055,951.

In order to be able to isolate the OBB acid contained in such complexes, with a view essentially to cyclize it into anthraquinone, these must be subjected, for example, to treatment with boiling water or sodium hydroxide. A treatment of this nature has the major disadvantage in that it causes destruction of the HF and of the BF$_3$ and consequently means that recovery of the HF/BF$_3$ catalyst used in the synthesis of anthraquinone described in the above-mentioned European Patent Application is not economically viable.

Prolonged heating of the complex at 150° C. to 200° C. makes decomposition possible, but at the same time causes almost total degradation of the OBB acid itself- moreover, the water water formed in the course of this degradation combines with the HF and the BF$_3$ and thus renders the catalyst unsuitable for direct recycling.

Prolonged heating of the complex under vacuum at a lower temperature, for example 50° C. to 100° C., makes it possible to limit the decomposition of the OBB acid, but allows some of the catalyst to remain in this OBB acid, which renders the process uneconomical.

Heating of the complex at a low temperature in an inert solvent still only leads to incomplete recovery of the catalyst and still causes significant degradation of the OBB acid.

French Patent Application No. 82/14,920 describes a process for the decomposition of the complex in which the complex is subjected to the action of an inert solvent at a temperature of at least 20° C. in a distillation column functioning with vigorous reflux of the solvent. Such a process allows virtually quantitative recovery of the HF and the BF$_3$, but has the disadvantage that the OBB acid can be isolated only after it has been separated from the solvent which acts on the complex.

SUMMARY OF THE INVENTION

The process according to the present invention overcomes the disadvantages of the known methods. The present invention, on the one hand, permits recovery of the HF and the BF$_3$ virtually quantitatively, and, on the other hand, the OBB acid is subjected to virtually no degradation and, simultaneously with the decomposition of the complex, can be cyclized to anthraquinone without being isolated from the medium in which it has been liberated and under the same conditions adopted to carry out the decomposition of the complex.

Briefly, the present invention consists of the process comprising subjecting the complex of the general formula (I) to the action of sulfuric acid in a concentration at least equal to 96% by weight, or to the action of an oleum, under atmospheric pressure or under a pressure lower than atmospheric pressure.

DETAILED DESCRIPTION

Figure 1:
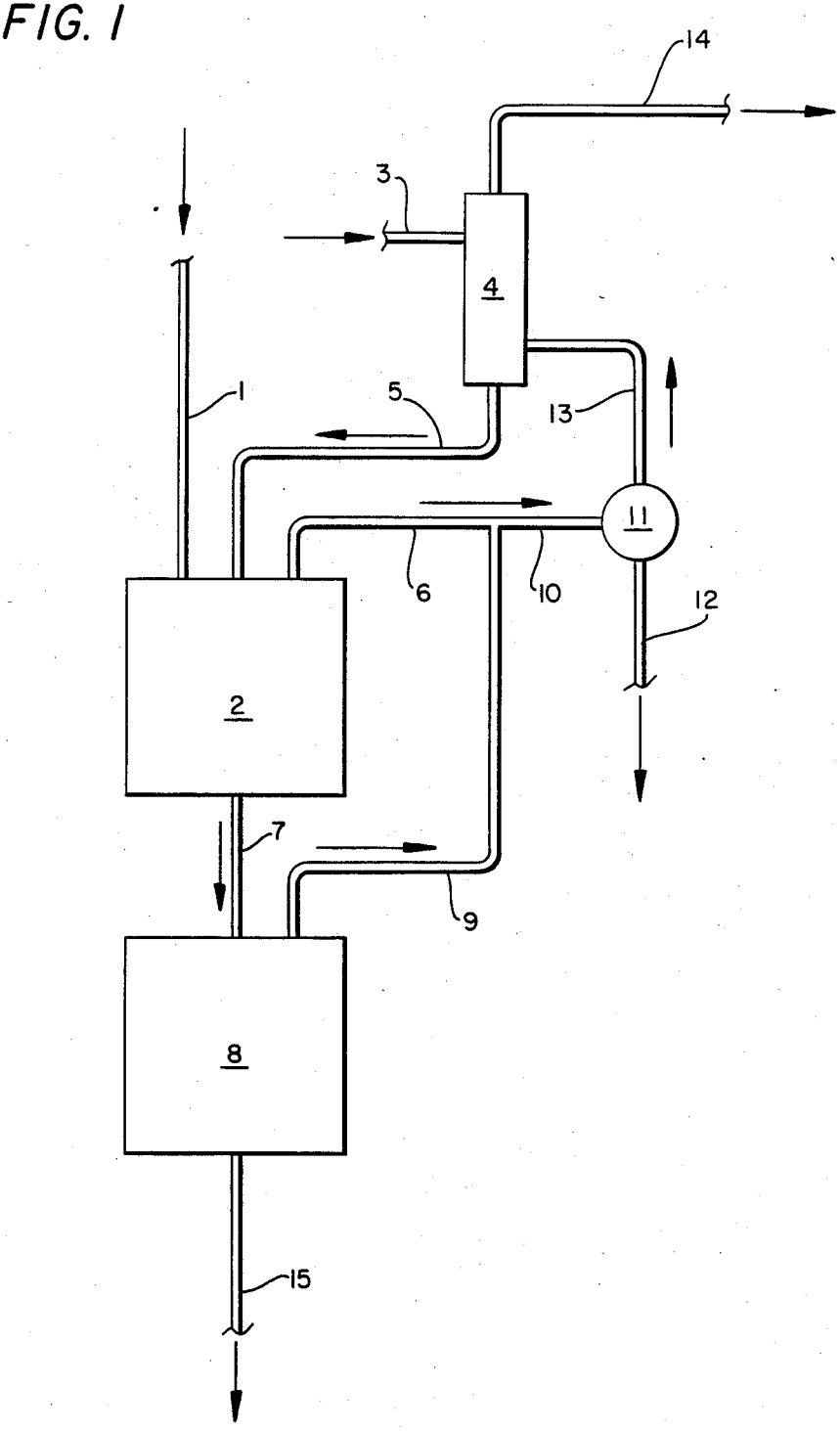
FIG. 1 is a schematic representation of a continuous process for the decomposition of a complex of orthobenzoyl-benzoic acid, hydrogen fluoride and boron trifluoride.

By way of example, the amount of sulfuric acid in a concentration equal to 96% by weight is preferably between 1 and 3 parts by weight per part of OBB acid in the complex, and that of oleum containing 20% by weight of SO$_3$ is 0.5 to 2 parts by weight per part of OBB acid.

The temperature at which the decomposition of the complex and the cyclization of the liberated OBB acid to anthraquinone are carried out is usually between about 100° C. and 180° C., preferably between 120° C. and 150° C.

To facilitate the recovery of the HF and of the BF$_3$, it is particularly advantageous to carry out the process in such a temperature range and under a pressure such that it will not be possible to detect escape of water from the reaction mixture. For example, the process will preferably be carried out under a pressure between atmospheric pressure and $4.10^{-2}$ bar.

The duration of the operation, in the context of the other conditions defined above, is generally between 15 minutes and 2 hours.

If the reaction is carried out under a pressure below atmospheric pressure, the use of sulfuric acid is preferred, the temperature chosen is preferably equal to 150° C. or slightly varied from this value and the duration of the operation is about 30 minutes.

If the reaction is carried out under atmospheric pressure or under a pressure below but close to this value, the use of an oleum, for example oleum containing 20% by weight of SO$_3$, is preferred to the use of sulfuric acid. The temperature is then about 120° C. and the duration of the operation is of the order of 1 hour.

In the course of the decomposition operation on the complex, the HF and the BF$_3$ are released in the gaseous state. The HF can be separated from the BF$_3$ by, for example, condensation. The HF and the BF$_3$ (the latter after sulfuric washing with the aid of, for example, the sulfuric acid or oleum used for the decomposition of the complex) can thus be re-used to produce the HF/BF$_3$ catalyst for the synthesis of the same complex.

In a particularly advantageous variant of the process, the HF liberated in the course of the decomposition operation on the complex can be partially or completely converted into BF$_3$ at the rate at which it is formed, by reaction with boric acid, H$_3$BO$_3$, which is introduced, for example, as a mixture with the oleum or the sulfuric acid.

The anthroaquinone formed during the decomposition operation on the complex can be easily and economically collected, for example by causing its precipitation by dilution of the final sulfuric mixture and by isolating and purifying the anthraquinone thus precipitated by simple filtration and washing operations. The dilution of the final sulfuric reaction mixture can be carried out with the aid of addition of water, or, more appropriately, with the aid of an aqueous solution of sulfuric acid in a concentration, for example, equal to or about 70% by weight, in a manner such that the concentration of sulfuric acid in the mixture containing the anthraquinone reaches about 80% by weight. The acid washings for the filtration can be reconcentrated for recycling into the decomposition operation on the complex, or they can be used to form the acid solution used to dilute the sulfuric solution of the anthraquinone.

The process according to the invention can be carried out continuously or discontinuously in one or more stirred reactors in series.

The single draiwng shows the schematic representation of the process corresponding to a continuous embodiment of the invention, in two stirred reactors in series: the complex of OBB acid, HF and BF3 of the general formula (I) is introduced via pipe 1 into the reactor 2. The concentrated sulfuric acid or the oleum led via pipe 3 passes through the washing column 4 before entering the reactor 2 via line 5. The HF and the BF3 leave the reactor 2 via pipe 6. The sulfuric solution present in the reactor 2 leaves the latter via line 7 and enters the reactor 8. The gaseous HF and BF3 leave the reactor 8 via pipe 9 and are recombined with the HF and BF3 circulating in line 6. The gaseous mixture thus formed enters 11, via pipe 10, where the HF is separated from the BF3 by condensation of the HF. The condensed HF is removed via line 12. The gaseous BF3 then enters the washing column 4, via line 13, from which it leaves via the BF3 take-off pipe 14. The sulfuric extract solution of reactor 8 is removed via pipe 15 for the purpose of, for example, the dilution, filtration, and washing operations which are described above and are carried out in apparatuses not shown in the single drawing.

The following examples, which are non-limiting, illustrate the invention according to the variant in which the HF liberated from the complex is converted quantitatively into BF3 by reaction with boric acid, H3BO3.

EXAMPLE 1

By a procedure according to the European Patent Application No. 0,055,951, 1 mole of phthalic anhydride and 1 mole of benzene are reacted, in proportion, in 10 moles of HF and 10 moles of BF3. After some of the BF3 is degassed at −40° C., a product is obtained, consisting of, for 1 mole of phthalic anhydride employed, a solution of the complex of the OBB acid in HF containing 203.3 g of OBB acid, 306.7 g of BF3, 200 g in total of HF and 22.7 g of impurities from the reaction, and the solution is evaporated in vacuum at 0° C. to give 60 g of final solution, from 100 g of the initial solution.

31.5 g of 96% strength by weight sulfuric acid and 8.5 g of boric acid, H3BO3 are added to these 60 g of solution, in a stirred stainless steel reactor, before then being heated, under a pressure of 4.10 bar, to 150° C., the mixture being maintained at this temperature for 20 minutes.

From the evaluation of the amount BF3 which leaves the reactor during the operation, it is concluded that the recovery yield of the HF and BF3 initially contained in the complex is more than 99%, which shows that the efficiency of the decomposition of the complex is virtually quantitative.

After cooling, precipitation, by dilution of the sulfuric mixture with water, of the anthraquinone produced from the OBB acid liberated from the complex, separation by filtration and washing of the anthraquinone thus precipitated, 23.6 g of pure anthraquinone are obtained, corresponding to a recovery of the OBB acid equal to at least 91.2%.

EXAMPLE 2

By treating, in the same apparatus and according to the same procedure as in Example 1, the same amount of the same evaporated solution of the complex as in Example 1 with 31.5 g of oleum containing 20% of SO3 at 120° C. under atmospheric pressure for 30 minutes in the presence of 8.5 g of boric acid, the recovery yield of the HF and BF3 initially contained in the complex is even greater than 99%, thus showing a virtually quantitative efficiency of the decomposition. The recovery yield of the OBB acid, calculated from the amount of pure anthraquinone collected after the operations of dilution of the final sulfuric mixture by 70% strength by weight sulfuric acid to precipitate the anthraquinone, filtration and washing of the precipitated anthraquinone, is 79%.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. Process for the decomposition of complexes of orthobenzoyl-benzoic acid, hydrogen fluoride and boron trifluoride of the general formula:

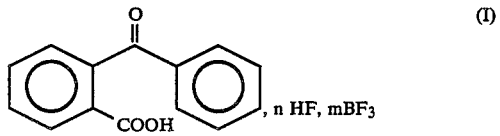

in which n and m are between 1 and 6 on the one hand for recovery of the hydrogen fluoride and the boron trifluoride, and, on the other hand, to obtain the anthraquinone resulting from cyclization of the orthobenzoyl-benzoic acid, the improvement comprising subjecting the said complex to the action of sulfuric acid in a concentration of at least about 96% by weight or of an oleum, under a pressure at most equal to atmospheric pressure and at a temperature between 100° C. and 180° C.

2. The process of claim 1, wherein the amount by weight of sulfuric acid is equal to 1 to 3 times that of the orthobenzoyl-benzoic acid contained in the complex.

3. The process of claim 1, wherein the amount by weight of oleum is equal to 0.5 to 2 times that of the orthobenzoyl-benzoic acid contained in the complex.

4. The process of claim 1, wherein the duration of the decomposition is between 15 minutes and 2 hours.

5. The process of claim 4, wherein the decomposition takes place in the presence of an amount of boric acid sufficient to convert at least some of the hydrogen fluoride contained in the complex into boron trifluoride.

6. The process of claim 5, wherein the final reaction mixture is diluted with water or an aqueous solution of sulfuric acid to precipitate the anthraquinone.

7. The process of claim 1, wherein the amount by weight of sulfuric acid is equal to 1 to 3 times that of the orthobenzoyl-benzoic acid contained in the complex and the duration of the decomposition is between 15 minutes and 2 hours.

8. The process of claim 1, wherein the amount by weight of oleum is equal to 0.5 to 2 times that of the orthobenzoyl-benzoic acid contained in the complex and the duration of the decomposition is between 15 minutes and 2 hours.

9. The process of claim 1, wherein the amount by weight of sulfuric acid is equal to 1 to 3 times that of the orthobenzoyl-benzoic acid contained in the complex, the duration of the decomposition is between 15 minutes and 2 hours, and the decomposition takes place in the presence of an amount of boric acid sufficient to convert at least some of the hydrogen fluoride contained in the complex into boron trifluoride.

10. The process of claim 1, wherein the amount by weight of oleum is equal to 0.5 to 2 times that of the orthobenzoyl-benzoic acid contained in the complex, the duration of the decomposition is between 15 minutes and 2 hours, and the decomposition takes place in the presence of an amount of boric acid sufficient to convert at least some of the hydrogen fluoride contained in the complex into boron trifluoride.

* * * * *